United States Patent [19]

Mattern et al.

[11] Patent Number: 5,578,588

[45] Date of Patent: Nov. 26, 1996

[54] MEDICAMENT FOR INCREASING THE TESTOSTERONE LEVEL

[75] Inventors: Claudia Mattern, Starnberg; Rüdiger Häcker, Herrsching, both of Germany

[73] Assignee: Arrowdean Ltd., Ireland

[21] Appl. No.: 335,729

[22] PCT Filed: Apr. 30, 1993

[86] PCT No.: PCT/DE93/00397

§ 371 Date: Nov. 7, 1994

§ 102(e) Date: Nov. 7, 1994

[87] PCT Pub. No.: WO93/21924

PCT Pub. Date: Nov. 11, 1993

[30] Foreign Application Priority Data

May 6, 1992 [DE] Germany .......................... 42 14 953.3

[51] Int. Cl.[6] .................................................. A61K 31/56
[52] U.S. Cl. .................................. 514/177; 514/182
[58] Field of Search ................................ 514/177, 182

[56] References Cited

U.S. PATENT DOCUMENTS

| | | | |
|---|---|---|---|
| 3,284,303 | 8/1966 | Meli | 167/74 |
| 4,877,774 | 10/1989 | Pitha et al. | 514/26 |
| 5,053,403 | 10/1991 | Orentreich et al. | 514/170 |

FOREIGN PATENT DOCUMENTS

0349091B1  5/1992  European Pat. Off. .

OTHER PUBLICATIONS

Vander et al., Human Physiology, 4th Ed., 1985.

*Primary Examiner*—Kimberly Jordan
*Attorney, Agent, or Firm*—Merchant, Gould, Smith, Edell, Welter & Schmidt, P.A.

[57] ABSTRACT

The invention concerns a drug for increasing the level of testosterone in the human body, the drug containing at least one testosterone precursor.

3 Claims, No Drawings

MEDICAMENT FOR INCREASING THE TESTOSTERONE LEVEL

This application is a 371 of PCT/DE93/00397 filed Apr. 30, 1993. The invention relates to a medicament for increasing the testosterone level in humans.

The main action of the steroid hormone testosterone is the intensifying of the primary and secondary sex characters of man, as well as the maintaining of the functions associated therewith. Apart from this main effect testosterone has a number of secondary effects, which are of great importance for the stressability and performance characteristics of the human organism. These include the maintaining of an anabolic metabolic situation, the restoration of the performance of man following exhausting exercise and increasing the psychophysiological stressability and stress resistance.

The action mechanisms of testosterone have been investigated in detail. The secondary effects on the psychophysiological state have, according to the latest research, been attributed to the presence of testosterone receptors in the central nervous system.

Over 90% of the testosterone in the blood is bound to protein and the biologically active component is free testosterone representing 4 to 8% of the total concentration in the blood. The testosterone concentration in the blood is subject to a physiological daily cycle (maximum concentration in the morning) a seasonal cycle (lowest concentration in May) and influences by living circumstances and ageing processes.

The overall testosterone concentration in the blood is individually very stable under normal conditions. High physical effort, long-lasting stress situations and unfavourable diet lower the blood level. With increasing age and in particular from about 35 in man there is a reduction of the free testosterone concentration. These changes lead to a reduced, general performance, to higher time requirements for restoring the organism after exhaustive exercise and to a reduction of the psychophysiological stressability and stress resistance. Research on physically and cyclically highly stressed persons have revealed that a rise in the testosterone level in the upper part of the individual physiological fluctuation range leads to a cancelling out of this negative situation and to an increase in the general performance characteristics. However, a concentration rise above the individual, upper standard limit leads to no better therapeutic effect and instead causes side effects.

The increase in the testosterone level in humans in the sense of a substitution has consequently become part of preventative and therapeutic concepts in old-age medicine, particularly for man. The supply conventionally takes place perorally or in an oily solution in intramuscular form and in part as a depot preparation.

However, the following disadvantages are associated with these administration forms:

the influencing of the blood level is overall difficult to control;

the individual starting situation and stress cannot be adequately taken into account for the medication;

peroral and intramuscular supply lead to a metabolization via the circulatory system liver—bile—intestine—liver ("first-pass effect");

this effect reduces the bioavailability and requires the supply of higher doses with the resulting higher stressing of the metabolism;

the supply of higher doses can lead to an undesired rise in the overall concentration, which via the physiological control mechanism reduces the endogenic testosterone production.

The problem of the present invention is therefore to provide a medicament for raising the testosterone level in humans, whose application is equivalent in its effect to the intramuscular supply of testosterone, which avoids the aforementioned disadvantages, requires a much lower dose and permits a stressing of the secondary action on the central nervous system.

According to the invention this problem is solved by a medicament having a content of at least one precursor of testosterone and which is preferably androstendione, progesterone or 17-α-hydroxy progesterone.

A particularly advantageous embodiment of the invention is characterized by a galenic preparation, which allows the supply by per nasal application using a dosing spray and having a preferred content of 3.5 to 15 mg of active substance per pump thrust.

Alternatively thereto the medicament according to the invention can also be in the form of a sustained release dragée, depot form or buccal tablet for peroral administration. In this case the preferred content per ingestion unit is 50 to 100 mg of active substance.

It has been shown that through the use of a precursor of testosterone, which is only transformed into the active substance in the organism, there is a more complex reaction of the steroid metabolism, which is more balanced and better corresponds to the physiological conditions, so that overall an optimum action can be obtained whilst avoiding side effects.

Animal tests carried out on the guinea pig have fundamentally proved the rapid transformation of radioactively labelled androstendione, progesterone or 17-α-hydroxy progesterone into testosterone.

In humans 50 to 100 mg of perorally supplied androstendione, progesterone or 17-α-hydroxy progesterone are also rapidly transformed into testosterone. In the case of androstendione supply e.g. after only 15 minutes in the blood there is a rise in the overall testosterone concentration from 40 to 83% (50 mg) or 111 to 237% (100 mg). There is an increase in the proportion of free, biologically active testosterone, the appearance of the concentration maximum and the path of the blood level in the case of a positive basic reaction reveal clear, repeating, individual differences.

In the case of the preferred pernasal administration by means of a dosing spray a single supply of 3.5 to 15 mg of androstendione, progesterone or 17-α-hydroxy progesterone led to testosterone level rises in the blood of 34 to 97%. The extent and time sequence thereof are comparable with the results which were obtainable in the case of the peroral supply of much higher doses or the intramuscular supply of testosterone propionate. Unlike in the case of peroral and intramuscular administration, with pernasal administration there was no significant "first-pass" metabolization of the precursor molecule.

This led to the good controllability of the influencing, which could be proved by multiple administrations. The individual reaction position is taken into account by the regulating mechanisms of the metabolism. An adapted increase of the free testosterone was obtained, whose extent and kinetics are comparable with the values obtained with peroral administration of a ten times higher dose.

A significant long-term effect was detected with multiple, pernasal administration. Three to four days following the final administration there was a further testosterone level increase of 48 to 97% in the blood and this was maintained for a further 6 to 7 days. This reaction is probably attributable to an influencing of the control cycle for endogenic testosterone production.

In addition, pernasal administration facilitates the transfer into the cerebrospinal fluid and also into other tissues and organs of the human organism. As the overcoming of the blood-brain barrier is a major problem for all pharmaceuticals acting on the central nervous system, the facilitated access to the cerebrospinal fluid via the pernasal administration represents a particular advantage of the medicament according to the invention. Thus, for the first time it is possible to influence the testosterone receptors in the brain, which represents a novel therapeutic approach for testosterone. The subsequently described improvement of the psychophysiological performance characteristics is probably due to the influencing of the central nervous system.

There is an increase in the testosterone/epitestosterone quotient in the metabolite profile of urine. However, it is not as marked in the case of pernasal administration (3.8 to max 14.3) and becomes normal on the day following the supply, whilst the testosterone level in the blood remains high.

The use of the nasal spray for 6 days (daily dose 5 to 7 mg) in physically and cyclically highly stressed persons in middle age led to a shortening of the regeneration following exhausting exercise and a better balanced metabolic situation. It must in particular be stressed that, unrequested, all the test persons reported a higher psychophysiological stressability and an improved stress resistance.

The features of the invention disclosed in the description and claims can be essential to the different embodiments of the invention, either singly or in random subcombinations.

We claim:

1. A method for increasing the level of testosterone in a human comprising nasal administration of at least one testosterone precursor.

2. The method according to claim 1, wherein the testosterone precursor is androstenedione, progesterone, 17-α-hydroxyprogesterone, or combinations thereof.

3. The method according to claim 1, wherein the nasal administration comprises administration of 3.5 to about 15 mg of testosterone precursor per pump thrust.

* * * * *